United States Patent [19]

Hewlett

[11] Patent Number: 4,559,183

[45] Date of Patent: Dec. 17, 1985

[54] PREPARATION OF CARBOXYLIC ACID ANHYDRIDES

[75] Inventor: Colin Hewlett, Middlesbrough, England

[73] Assignee: The Halcon SD Group, Inc., New York, N.Y.

[21] Appl. No.: 644,294

[22] Filed: Aug. 27, 1984

Related U.S. Application Data

[63] Continuation of Ser. No. 467,977, May 8, 1974 and a Continuation of Ser. No. 826,810, Aug. 22, 1977, abandoned, which is a continuation-in-part of Ser. No. 394,220, Sep. 4, 1973, abandoned.

[51] Int. Cl.$^4$ .............................................. C07C 51/12
[52] U.S. Cl. ..................................... 260/546; 260/549
[58] Field of Search ............................... 260/546, 549

[56] References Cited

U.S. PATENT DOCUMENTS

| | | | |
|---|---|---|---|
| 2,727,902 | 12/1955 | Reppe | 260/546 |
| 2,729,651 | 1/1956 | Rëppe | 260/546 |
| 2,730,546 | 1/1956 | Rëppe | 260/546 |
| 2,789,137 | 4/1957 | Reppe | 260/546 |
| 3,717,670 | 2/1973 | Schultz | 260/546 |
| 3,819,669 | 6/1974 | Knipton | 260/546 |
| 3,821,265 | 6/1974 | Forster | 260/546 |
| 3,842,788 | 7/1975 | Knipton | 260/546 |
| 3,852,346 | 12/1974 | Förster | 260/546 |
| 3,856,856 | 12/1974 | Nazuki | 260/546 |
| 3,927,078 | 12/1975 | Lapporte | 260/546 |
| 4,046,807 | 6/1977 | Kuckertz | 26/546 |

*Primary Examiner*—Robert Gerstl
*Attorney, Agent, or Firm*—William C. Long; Riggs T. Stewart; Harold N. Wells

[57] ABSTRACT

A carboxylic acid anhydride such as acetic anhydride, is prepared from a carboxylate ester or a hydrocarbyl ether in processes comprising the use of a halide, carbon monoxide and a Group VIII noble metal.

16 Claims, No Drawings

PREPARATION OF CARBOXYLIC ACID ANHYDRIDES

REFERENCE TO RELATED APPLICATION

This is a continuation of application Ser. No. 826,810 filed Aug. 22, 1977, which is a continuation-in-part of co-pending application, Ser. No. 394,220, filed Sept. 4, 1973 both abandoned.

This invention relates to the preparation of the anhydrides of carboxylic acids, more particularly mono-carboxylic acids, and especially the anhydrides of lower alkanoic acids, such as acetic anhydride, by carbonylation.

Acetic anhydride has been known as an industrial chemical for many years and large amounts are used in the manufacture of cellulose acetate. It has commonly been produced on an industrial scale by the reaction of ketene and acetic acid. It is also known that acetic anhydride can be produced by the decomposition of ethylidene diacetate, as well as by the oxidation of acetaldehyde, for example. Each of these "classic" processes has well known drawbacks and disadvantages and the search for an improved process for the production of acetic anhydride has been a continuing one. Proposals for producing anhydrides by the action of carbon monoxide upon various reactants (carbonylation) have been described, for example, in Reppe et al. U.S. Pat. Nos. 2,729,561; 2,730,546 and 2,789,137. However, such prior proposals involving carbonylation reactions have required the use of very high pressures. Carbonylation at lower pressures has been proposed but as a route to the preparation of acetic acid. French Pat. No. 1,573,130, for example, describes the carbonylation of methanol and mixtures of methanol with methyl acetate in the presence of compounds of iridium, platinum, palladium, osmium and ruthenium and in the presence of bromine or iodide under more moderate pressures than those contemplated by Reppe et al. Similarly, South African Pat. No. 68/2174 produces acetic acid from the same reactants using a rhodium component in combination with bromine or iodide. More recently, Schultz (U.S. Pat. Nos. 3,689,533 and 3,717,670) has disclosed a vapor-phase process for acetic acid production employing various catalysts comprising a rhodium component dispersed on a carrier. None of these relatively recent carbonylation disclosures, however, refers to or contemplates the preparation of acetic anhydride or other carboxylic acid anhydrides.

It is, therefore, an object of the present invention to provide an improved process for the manufacture of carboxylic acid anhydrides, especially lower alkanoic anhydrides, such as acetic anhydride.

It is a further object of the invention to provide an improved process for the manufacture of carboxylic acid anhydrides wherein the high pressures of the prior art are not required.

In accordance with this invention, an acyl halide which is an iodide or a bromide, such as acetyl iodide, which can be suitably produced by the carbonylation of a hydrocarbyl halide, especially a lower alkyl halide, which is an iodide or a bromide, such as methyl iodide, is reacted with a carboxylate ester, especially a lower alkyl alkanoate, or a hydrocarbyl ether such as a lower alkyl ether, to produce a carboxylic acid anhydride, such as a lower alkanoic anhydride, and regenerate the halide. Thus, acetic anhydride, for example, can be effectively prepared by reacting acetyl iodide with methyl acetate. The acetyl iodide, in turn, can be prepared by reacting methyl iodide with carbon monoxide at moderate CO partial pressures, this carbonylation reaction being carried out in the presence of a Group VIII noble metal catalyst. In the foregoing reactions the iodides may be replaced by the corresponding bromides. In like manner, other lower alkanoic anhydrides, i.e., anhydrides of lower alkanoic acids, such as propionic anhydride, butyric anhydrides and valeric anhydrides, can be produced by reacting the corresponding acyl halide, such as propionyl iodide, propionyl bromide, the butyryl iodides, the butyryl bromides, etc., with a lower alkyl alkanoate or a lower alkyl ether. Similarly, other carboxylic acid anhydrides, e.g. the anhydrides of other alkanoic acids, such as those containing up to 12 carbon atoms, for example caprylic anhydrides, capric anhydrides and lauric anhydrides, or the anhydrides of monocyclic aromatic monocarboxylic acids, such as benzoic acid, can be produced. As in the case of the lower alkanoic anhydrides, these higher anhydrides are produced by reacting the corresponding acyl halide such as caprylyl iodide, caprylyl bromide, decanoyl iodide, decanoyl bromide, dodecanoyl iodide, dodecanoyl bromide, benzoyl bromide, benzoyl iodide, and the like, with appropriate esters, e.g. alkyl alkanoates containing up to 11 carbon atoms in the alkyl group and up to 12 carbon atoms in the carboxylate or acyl group, or aryl esters, or corresponding ethers, such as heptyl caprylate, nonyl caproate, undecyl laurate, phenyl benzoate, heptyl ether, nonyl ether, phenyl ether, and the like. In each case, as described above in connection with the lower alkanoic anhydrides, the acyl halide can be readily prepared by reacting the corresponding alkyl or aryl halide with carbon monoxide in the presence of a Group VIII noble metal catalyst to effect a carbonylation reaction.

It is preferred that the reactants be selected so that the resulting anhydride will be a symmetrical anhydride, i.e., having two identical acyl groups, viz. wherein R in equations (1) and (2) or (1) and (3) is the same in each instance, but it is within the scope of the invention to produce non-symmetrical or mixed anhydrides and this can be readily effected by using different combinations of reactants, e.g. by using compounds having different R groups in the foregoing reactions, as will be obvious to persons skilled in the art.

The above-described reactions can be expressed as follows:

$$RX + CO \rightarrow RCOX \tag{1}$$

$$RCOX + RCOOR \rightarrow RX + (RCO)_2O \tag{2}$$

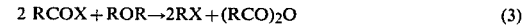

$$2\,RCOX + ROR \rightarrow 2RX + (RCO)_2O \tag{3}$$

wherein R is a hydrocarbyl radical which may be saturated, e.g. alkyl of 1 to 11 carbon atoms, or monocyclic aryl, e.g. phenyl, or alkaryl, e.g. benzyl. Preferably R is lower alkyl, i.e., an alkyl group of 1 to 4 carbon atoms, such as methyl, ethyl, n-propyl, i-propyl, n-butyl, sec-butyl, i-butyl and t-butyl, and X is I or Br. The hydrocarbyl radical may be substituted with substituents which are inert in the reactions of the invention.

The more volatile alkyl halide and unreacted acyl halide and ether or ester in the final product mixture can be readily removed, as by distillation, for recycling, and the net yield of product is substantially exclusively the desired carboxylic anhydride. In the case of liquid-phase reaction, which is preferred, the organic compounds are easily separated from the noble metal catalyst, as by distillation. It has been discovered that the process can not only be carried out in two reaction stages, i.e., a first stage wherein the hydrocarbyl halide is carbonylated in the presence of a Group VIII noble metal catalyst and a second stage wherein the carbonylation product (acyl halide) is reacted with the ester or ether, but the two stages can be advantageously combined in a single reaction zone to which the carbon monoxide, the ester or ether, the hydrocarbyl halide and the noble metal catalyst are fed so that the process can, in effect, be carried out in a single stage. No water is produced in the above-described reactions and anhydrous or substantially anhydrous reactants are employed since it is important to operate under substantially anhydrous conditions.

Thus, when the acyl halide is produced by carbonylation and the process is carried out in two stages, a hydrocarbyl halide, e.g., methyl iodide, and carbon monoxide are reacted in a first reaction zone in the presence of a Group VIII noble metal catalyst to produce an acyl halide, e.g., acetyl iodide, which is then transferred to a second reaction zone and the acyl halide is there reacted with the ester, e.g., a lower alkanoic ester, or a hydrocarbyl ether, e.g., a lower alkyl ether to produce product carboxylic anhydride and to regenerate hydrocarbyl halide. The hydrocarbyl halide is then separated from the product anhydride, as by distillation, and recycled to the first-stage reaction zone for carbonylation, unreacted acyl halide and ester or ether also being recycled, and the carboxylic anhydride is recovered as the only net product.

In carrying out the reaction between the hydrocarbyl halide and carbon monoxide, temperatures over a wide range, e.g., 20° to 500° C. are suitable but temperatures of 100° to 350° C. are preferably employed and the more preferred temperatures generally lie in the range of 125° to 250° C. Temperatures lower than those mentioned can be used but they tend to lead to reduced reaction rates, and higher temperatures may also be employed but there is no particular advantage in their use. The time of reaction is not a parameter of the process and it will, to a large extent, depend upon the temperature employed, but typical residence times by way of example, will generally fall in the range of 0.1 to 20 hours. The reaction is, of course, carried out under superatmospheric pressures, but one of the features of the invention is that excessively high pressures are not necessary, although they can be employed, if desired. In general, the reaction is effectively carried out by employing a carbon monoxide partial pressure which is preferably 5 to 2000 p.s.i.g., and most preferably 25 to 1000 p.s.i.g. but which may, if desired, range from 0.1 to 15,000 p.s.i.g. When a liquid-phase reaction is employed, the total pressure is that required to maintain the desired liquid phase. Thus, the liquid-phase reaction is conveniently carried out in an autoclave or similar apparatus. At the end of the desired residence time, the reaction mixture is transferred to a second reaction zone and heated. Preferably, the reaction product first is introduced into a distillation zone, which may be a fractional distillation column, effective to separate any unreacted hydrocarbyl halide that may be present, and to separate the acyl halide from the catalyst. The catalyst and the hydrocarbyl halide can then be recycled to the first-stage reaction zone. Alternatively, these separations can be omitted and the entire reaction mixture can be transferred to the second-stage reaction zone, or only the hydrocarbyl halide or only the catalyst can be separated at this point.

In the second reaction zone, the acyl halide is reacted with a carboxylic acid ester or hydrocarbyl ether. This reaction may be carried out thermally if the acyl halide has been separated from the Group VIII noble metal catalyst, or if this separation has not been made, then the reaction with the ester or ether can take place in the presence of the catalyst. In either case, a temperature in the range of 0° to 300° C. is suitably employed, with a temperature in the range of 20° to 250° C. being preferred and a temperature of 50° to 200° C. being the most desirable. In the course of the reaction, carboxylic anhydride is formed and the hydrocarbyl halide is regenerated. The resultant product mixture will then contain the product anhydride and hydrocarbyl halide and it may also contain unreacted ester or ether and acyl halide, plus noble metal catalyst if the separation of catalyst was not made prior to the second-stage reaction. The organic constituents are readily separated from one another by conventional fractional distillation, the hydrocarbyl halide generally being the most volatile and the anhydride generally being the least volatile, and the anhydride being easily distilled away from the inorganic catalyst, if present. The recovered hydrocarbyl halide is then suitably recycled to the first-stage reaction zone for carbonylation, along with any recovered catalyst. Any unreacted ester or ether and/or acyl halide can be recycled to the second-stage reaction zone, and the remaining organic constituent of the reaction mixture, the carboxylic acid anhydride, is recovered as product.

In accordance with the preferred embodiment of the invention, the two reaction stages described above are combined, i.e., the process is carried out in a single reaction zone in which a halide source e.g. the hydrocarbyl halide, fed to the first reaction zone and the carboxylate ester or hydrocarbyl ether fed to the second reaction zone in the two-stage embodiment, are both charged to a single reaction zone and are heated together, preferably in the liquid phase, in the presence of carbon monoxide and in the presence of the Group VIII noble metal catalyst. It will be understood that the hydrocarbyl halide may be formed in situ and the halide may thus be supplied to the system not only as the hydrocarbyl halide but the halogen moiety may also be supplied as another organic halide or as the hydrohalide or other inorganic halide e.g. salts, such as the alkali metal or other metal salts, or even as elemental iodine or bromine. Following the reaction the several components of the reaction mixture are readily separated from one another, as by fractional distillation.

In carrying out the one-stage embodiment of the invention, a wide range of temperatures, e.g. 20° to 500° C. are suitable but temperatures of 100° to 300° C. are preferably employed and the more preferred temperatures generally lie in the range of 125° to 250° C. As in the case of the two-stage embodiment, temperatures lower than those mentioned can be used but they tend to lead to reduced reaction rates, and higher temperatures may also be employed but there is no particular advantage in their use. The time of reaction is also not a parameter of the one-stage process and depends largely upon the temperature employed, but typical residence times, by way of example, will generally fall in the range of 0.1 to 20 hours. The reaction is carried out under super-atmospheric pressure but, as previously mentioned, it is a feature of the invention that excessively high pressures, which require special high-pressure equipment, are not necessary. In general, the reaction is effectively carried out by employing a carbon monoxide partial pressure which is preferably 5 to 2000 p.s.i.g., and most preferably 25 to 1000 p.s.i.g., although carbon monoxide partial pressures of 0.1 to 15,000 p.s.i.g. can also be employed. The total pressure is preferably that required to maintain the liquid phase and in this case the reaction can be advantageously carried out in an autoclave or similar apparatus. At the end of the desired residence time, the reaction mixture is separated into its several constituents, as by distillation. Preferably, the reaction product is introduced into a distillation zone, which may be a fractional distillation column, or a series of columns, effective to separate the hydrocarbyl halide, acyl halide and ester or ether from the product anhydride. The boiling points of these several compounds are sufficiently far apart that their separation by conventional distillation presents no particular problem. Likewise, the anhydride can be readily distilled away from the noble metal catalyst. The hydrocarbyl halide and the noble metal catalyst, as well as acyl halide, can then be combined with fresh amounts of ester or ether and carbon monoxide and reacted to produce additional quantities of anhydride.

The final reaction mixture will normally contain the acyl halide along with the product anhydride and it is a feature of the discovery underlying the invention that this acyl halide, after separation from the anhydride, can be reacted with the ester or ether either by recycling to the reaction or by reacting the ester or ether and the acyl halide separately, as in the second stage of the two-stage embodiment described above (equations 2 and 3), to produce additional amounts of anhydride.

The ratio of ester or ether to the halide in the reaction system can vary over a wide range. Typically, there are used 1 to 500 equivalents of the ester or ether per equivalent of halide, preferably 1 to 200 equivalents per equivalent. Thus, in the case of an ester there are typically used 1 to 500 mols, preferably 1 to 200 mols of ester per mol of halide reactant, and in the case of an ether 0.5 to 250, preferably 0.5 to 100 mols per mol of halide. By maintaining the partial pressure of carbon monoxide at the values specified, adequate amounts of the reactant are always present to react with the hydrocarbyl halide.

The hydrocarbyl halide carbonylation (equation 1) discussed above in connection with the two-stage embodiment is advantageously carried out in the presence of a solvent or diluent. While this solvent or diluent can be an organic solvent which is inert in the environment of the process, it can also be a carboxylate ester or a hydrocarbyl ether and thus carboxylic acid anhydride will be produced along with the acyl halide which is the desired product in that instance. In other words, the acyl halide-forming reaction of the two-stage embodiment will then take on the character of the one-stage embodiment. Similarly, the one-stage embodiment is advantageously carried out in the presence of a solvent or diluent, particularly when the reactant has a relatively low boiling point, as in the case of ethyl ether. The presence of a higher boiling solvent or diluent, which may be the product anhydride itself, e.g. acetic anhydride in the case of ethyl ether, or which may be the corresponding ester, e.g. methyl acetate, again in the case of methyl ether, will make it possible to employ more moderate total pressure. Alternatively, the solvent or diluent may be any organic solvent which is inert in the environment of the process such as hydrocarbons, e.g. octane, benzene, toluene, or carboxylic acids, e.g. acetic acid, and the like. A solvent or diluent is suitably selected which has a boiling point sufficiently different from the components of the reaction mixture that it can be readily separated, as will be apparent to persons skilled in the art.

The Group VIII noble metal catalyst, i.e., iridium, osmium, platinum, palladium, rhodium and ruthenium, can be employed in any convenient form viz. in the zero valent state or in any higher valent form. For example, the catalyst to be added may be the metal itself in finely divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Similarly complexes of the metals can be employed, for example the metal carbonyls, such as iridium carbonyls and rhodium carbonyls, or as other complexes such as the carbonyl halides, e.g., iridium tri-carbonyl chloride $[Ir(CO)_3Cl]_2$ or the acetylacetonates, e.g., rhodium acetylacetonate $Rh(C_5H_7O_2)_3$.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like the other reactants, should, however, be essentially dry, i.e., the CO and the other reactants should be reasonably free from water. The presence of minor amounts of water such as may be found in the commercial forms of the reactants is, however, entirely acceptable.

It has been surprisingly found that the activity of the Group VIII noble metal catalysts described above can be significantly improved, particularly with respect to reaction rate and product concentration, by the concurrent use of a promoter. Effective promoters include the elements having atomic weights greater than 5 of Groups IA, IIA, IIIA, IVB, VIB, the non-noble metals of Groups VIII and the metals of the lanthanide and actinide groups of the Periodic Table. Particularly preferred are the lower atomic weight metals of each of these groups, e.g. those having atomic weights lower than 100, and especially preferred are the metals of Groups IA, IIA and IIIA. In general, the most suitable elements are lithium, magnesium, calcium, titanium, chromium, iron, nickel and aluminum. Most preferred are lithium, aluminum and calcium, especially lithium. The promoters may be used in their elemental form e.g. as finely-divided or powdered metals, or they may be employed as compounds of various types, both organic and inorganic, which are effective to introduce the element into the reaction system. Thus, typical compounds of the promoter elements include oxides, hydroxides, halides, e.g. bromides and iodides, oxyhalides, hydrides, alkoxides, and the like. Especially preferred organic compounds are the salts of organic mono-carboxylic acids e.g. alkanoates such as acetates, butyrates, decanoates and laurates, benzoates, and the like. Other compounds include the metal alkyls, carbonyl compounds as well as chelates, association compounds and enol salts. Particularly preferred are the elemental forms, compounds which are bromides or iodides, and organic salts e.g. salts of the mono-carboxylic acid corresponding to the anhydride being produced. Mixtures of promoters can be used, if desired, especially mixtures of elements from different Groups of the Periodic Table. The exact mechanism of the effect of the promoter, or the exact form in which the promoter acts, is not known but it has been noted that when the promoter is added in elemental form, e.g. as a finely-divided metal, a slight induction period is observed.

The quantity of promoter can vary widely but preferably it is used in the amount of 0.0001 mol to 100 mols per mol of Group VIII noble metal catalyst, most preferably 0.001 to 10 mols per mol of catalyst.

In the working up of the reaction mixtures, e.g. by distillation, as discussed above, the promoter generally remains with the Group VIII noble metal catalyst, i.e. as one of the least volatile components, and is suitably recycled or otherwise handled along with the catalyst.

Reaction (3) has been found to proceed in two stages, as follows:

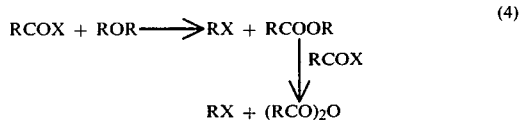

The reaction between the acyl halide and the hydrocarbyl ether can, therefore, in accordance with one aspect of this invention, be used to prepare the corresponding ester, which can be removed from the system as a recoverable intermediate, if desired. Since the promoter tends to favor the formation of the anhydride, i.e. it increases the rate of the second reaction of equation (4), when it is desired to recover the intermediate ester, a promoter should not be used.

It will be apparent that the above-described reactions, whether carried out in one stage or in two stages, lend themselves readily to continuous operation in which the reactants and catalyst, preferably in combination with a promoter, are continuously supplied to the appropriate reaction zone and the reaction mixture continuously distilled to separate the volatile organic constituents and to provide a net product consisting essentially of carboxylic acid anhydride, with the other organic components being recycled and, in the case of liquid-phase reaction, a residual Group VIII noble metal-containing (and promoter-containing) fraction also being recycled. In the case of such continuous operation, it will be apparent that the halogen moiety remains in the system at all times subject only to occasional handling losses or purges. The small amount of halogen makeup which may be needed from time to time is preferably effected by supplying the halogen in the form of the hydrocarbyl halide but, as pointed out above, the halogen moiety may also be supplied as another organic halide or as the hydrogen halide or other inorganic halide, e.g. salts, such as the alkali metal or other metal salts, or as elemental iodine or bromine.

As previously indicated, the carbonylation reaction involved in the process of the invention can be carried out in the vapor phase, if desired, by appropriate conrol of the total pressure in relation to the temperature so that the reactants are in vapor form when in contact with the catalyst. In the case of vapor phase operation, and in the case of liquid-phase operation, if desired, the catalyst and promoter, i.e. the catalyst components, may be supported, i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst, or the catalyst and promoter, followed by drying. Catalyst component concentrations upon the carrier may vary widely, e.g., 0.01 weight percent to 10 weight percent, or higher.

The following examples will serve to provide a fuller understanding of the invention, but it is to be understood that they are given for illustrative purposes only, and are not to be construed as limitative of the invention. In the examples, all parts and percentages are by weight, unless otherwise indicated.

EXAMPLE 1

Methyl acetate (3.7 parts) and acetyl iodide (8.5 parts) are heated together at reflux for 4 hours. The reflux condenser is maintained at a temperature of 45°–50° C. and the uncondensed vapor from this condenser is condensed in a second condenser maintained at 10° C. Methyl iodide (2.8 parts) together with minor amounts (about 15%) of methyl acetate are collected from the second condenser and the mixture remaining in the still contains 20% by weight of acetic anhydride (2.2 parts) as determined by GC analysis. The remainder of the still mixture consists of unreacted methyl acetate and acetyl iodide, along with minor amounts of methyl iodide.

EXAMPLE 2

Methyl iodide (71 parts) and rhodium trichloride hydrate (0.83 part) are heated in admixture with 300 parts of methyl acetate at 175°–200° C. in a stirred stainless steel autoclave fitted with a Hastelloy B liner under an atmosphere of carbon monoxide (CO partial pressure 730–590; total pressure 1000 p.s.i.g.). After 3 hours reaction time, 0.7 mole of carbon monoxide per mole of methyl iodide has been absorbed and GC analysis of the reaction mixture showed that it contained 7.7% acetyl iodide and 8.7% acetic anhydride. The remainder of the reaction mixture consists of unreacted reagents and catalyst. The autoclave is cooled and vented and the reaction mixture discharged. The reaction mixture is then diluted with 100 parts of nonane to facilitate separation and distilled at atmospheric pressure through a 15-plate Oldershaw column. Methyl iodide and methyl acetate are distilled at a head temperature of 45°–57° C. and then an acetyl iodide cut (18.7 parts) b. 108°–111° C. is taken followed by a two-phase acetic anhydride-nonane cut b. 113°–127.5° C. The lower phase is separated (21.6 parts) and identified as essentially pure acetic anhydride by GC analysis and infrared spectroscopy. The acetyl iodide thus formed is appropriately used for the reaction of Example 1.

EXAMPLE 3

Methyl acetate (300 parts), methyl iodide (35 parts) and rhodium chloride hydrate (1.6 parts) are heated at 200° C. in a stirred stainless steel autoclave fitted with a Hastelloy B liner under an atmosphere of carbon monoxide (total pressure 1000 p.s.i.g.; partial pressure of carbon monoxide 590 p.s.i.g.). After 2 hours reaction time, 0.46 mole of carbon monoxide per 0.246 mole of methyl iodide has been absorbed and GC analysis of the reaction mixture shows it to contain 15.3% acetic anhydride (40 parts) along with 4.5% acetyl iodide (11.9 parts). The remainder of the reaction mixture is composed of unreacted reagents and catalyst.

EXAMPLE 4

Methyl acetate (6 parts), methyl iodide (0.7 part) and rhodium chloride (0.1 part) are heated in an atmosphere of carbon monoxide (initial partial pressure 300 p.s.i.g.) at 175° C. for 16 hours in a rotating glass-lined pressure vessel. GC analysis of the reaction mixture showed that it contained 10% acetic anhydride (0.6 part) and 2.8% acetyl iodide (0.17 part). The remainder of the reaction mixture is as described in Examples 2 and 3.

EXAMPLE 5

Methyl acetate (6 parts), methyl iodide (0.7 part) and iridium iodide (0.1 part) are heated in an atmosphere of carbon monoxide (initial partial pressure 350 p.s.i.g.) at 175° C. for 16 hours in a rotating glass-lined pressure vessel. GC analysis of the reaction mixture shows that it contains 15% acetic anhydride (0.9 part) and 2.8% acetyl iodide (0.17 part) in admixture with unreacted reactants and catalyst.

EXAMPLE 6

Examples 1–5 are repeated but using acetyl bromide and methyl bromide in place of acetyl iodide and methyl iodide respectively. Corresponding results are obtained in terms of reaction products, but the conversions are considerably lower.

EXAMPLE 7

Examples 1–5 are repeated but using ethyl propionate, propionyl iodide and ethyl iodide in place of methyl acetate, acetyl iodide and methyl iodide, respectively. Propionic anhydride is produced in corresponding manner, with propionyl iodide also being produced in the procedures of runs 2–5.

EXAMPLE 8

Examples 1–5 are repeated but using an equivalent amount of dimethyl ether in place of the methyl acetate. Corresponding production of acetic anhydride and acetyl iodide is observed.

EXAMPLE 9

Methyl acetate (300 parts), dimethyl ether (182 parts), lithium iodide (8.8 parts), methyl iodide (65 parts), rhodium trichloride hydrate (3 parts) and chromium metal powder (3 parts) are heated at 150° C. in a stirred stainless-steel autoclave under an atmosphere of carbon monoxide (total pressure 800 p.s.i.g.; initial partial pressure of carbon monoxide 125 p.s.i.g.). After 10 hours reaction time GC analysis of the reaction mixture shows it to contain 54% acetic anhydride (407 parts) and 31% methyl acetate (233 parts). The remainder of the reaction mixture is composed of unreacted reagents, reaction intermediates and catalyst components.

EXAMPLE 10

Example 9 is repeated but using an equivalent amount of lithium iodide in place of the methyl iodide and the chromium metal powder. Corresponding production of acetic anhydride and methyl acetate is observed.

EXAMPLE 11

Dimethyl ether (187 parts), acetic anhydride (408 parts), lithium iodide (70 parts) and rhodium trichloride hydrate (3 parts) are heated at 150° C. in a stirred stainless steel autoclave under an atmosphere of carbon monoxide (total pressure 650 p.s.i.g.; initial partial pressure of carbon monoxide 40 p.s.i.g.). After 10 hours reaction time GC analysis of the reaction mixture shows it to contain 64% acetic anhydride (498 parts) and 21.5% methyl acetate (167 parts).

EXAMPLE 12

Methyl acetate (150 parts), rhodium trichloride hydrate (0.75 part) iodine (18.5 parts) and chromium metal powder (3 parts) are heated at 175° C. in a stirred glass-lined pressure vessel, under an atmosphere of carbon monoxide (total pressure 350 p.s.i.g.; initial partial pressure of carbon monoxide 66 p.s.i.g.). After 4 hours reaction time GC analysis of the reaction mixture shows it to contain 59% acetic anhydride (121 parts). In this and the following examples, wherein the product anhydride analysis is given, the remainder of the reaction mixture in each case is composed of unreacted reagent, reaction intermediates and catalyst components, unless otherwise indicated.

EXAMPLE 13

Methyl acetate (600 parts), methyl iodide (65 parts), lithium iodide (9 parts), chromium metal powder (3 parts) and rhodium chloride (3 parts) are heated at 175° C. in a stainless-steel autoclave under an atmosphere of carbon monoxide (total pressure 350 p.s.i.g.; initial partial pressure of carbon monoxide 66 p.s.i.g.). After 8 hours reaction time a GC analysis of the reaction mixture shows it to contain 71.1% acetic anhydride (601 parts).

EXAMPLE 14

Methyl acetate (150 parts), rhodium trichloride hydrate (0.75 part), aluminum iodide (17.5 parts) and chromium metal powder (one part) are heated at 175° C. in a stirred glass-lined pressure vessel, under an atmosphere of carbon monoxide (total pressure 350 p.s.i.g., initial partial pressure of carbon monoxide 66 p.s.i.g.). After 4 hours reaction time GC analysis of the reaction mixture shows it to contain 67.6% acetic anhydride (141 parts).

EXAMPLE 15

Methyl acetate (150 parts), rhodium trichloride hydrate (0.75 part), magnesium iodide (17.5 parts) and chromium metal powder (one part) are heated at 175° C. in a stirred glass-lined pressure vessel, under an atmosphere of carbon monoxide (total pressure 350 p.s.i.g.; initial partial pressure of carbon monoxide 66 p.s.i.g.). After 4 hours reaction time GC analysis of the reaction mixture shows it to contain 40% acetic anhydride (76 parts).

EXAMPLE 16

Methyl acetate (150 parts), rhodium trichloride hydrate (0.75 part) and anhydrous chromous iodide (20 parts) are heated at 175° C. in a stirred glass-lined pressure vessel, under an atmosphere of carbon monoxide (total pressure 350 p.s.i.g.; initial partial pressure of carbon monoxide 66 p.s.i.g.). After 4 hours reaction time GC analysis of the reaction mixture shows it to contain 52.2% acetic anhydride (104 parts).

EXAMPLE 17

Methyl acetate (150 parts), rhodium trichloride hydrate (0.75 part), methyl iodide (18.5 parts), chromium metal powder (one part) and titanium dioxide (3 parts) are heated at 175° C. in a stirred glass-lined pressure vessel, under an atmosphere of carbon monoxide (total pressure 350 p.s.i.g.; initial partial pressure of carbon monoxide 66 p.s.i.g.). After 4 hours reaction time GC analysis of the reaction mixture shows it to contain 39% acetic anhydride (81 parts).

EXAMPLE 18

Methyl acetate (150 parts), rhodium trichloride hydrate (0.75 part), methyl iodide (18.5 parts) and chromium carbonyl (5.7 parts) are heated at 175° C. in a stirred glass-lined pressure vessel, under an atmosphere of carbon monoxide (total pressure 350 p.s.i.g.; initial partial pressure of carbon monoxide 66 p.s.i.g.). After 4 hours reaction time GC analysis of the reaction mixture shows it to contain 51% acetic anhydride (103 parts).

EXAMPLE 19

Methyl acetate (150 parts), rhodium trichloride hydrate (0.75 part), methyl iodide (18.5 parts) and chromium metal powder (3 parts) are heated at 175° C. in a stirred glass-lined pressure vessel, under an atmosphere of carbon monoxide (total pressure 350 p.si.g.; initial partial pressure of carbon monoxide 66 p.s.i.g.). After 4 hours reaction time GC analysis of the reaction mixture shows it to contain 56.5% acetic anhydride (115 parts).

EXAMPLE 20

Methyl acetate (150 parts), rhodium trichloride hydrate (0.75 part), chromium metal powder (one part), aluminum oxide (2.5 parts) and methyl iodide (18.5 parts) are heated at 175° C. in a stirred glass-lined pressure vessel, under an atmosphere of carbon monoxide (total pressure 350 p.si.g.; initial partial pressure of carbon monoxide 66 p.s.i.g.). After four hours reaction time GC analysis of the reaction mixture shows it to contain 59% acetic anhydride (122 parts).

EXAMPLE 21

Methyl acetate (150 parts), rhodium trichloride hydrate (0.75 part), methyl iodide (37 parts), chromium carbonyl (2.2 parts) and aluminum oxide (one part) are heated at 175° C. in a stirred glass-lined pressure vessel, under an atmosphere of carbon monoxide 66 p.s.i.g.). After three hours reaction time GC analysis of the reaction mixture shows it to contain 56% acetic anhydride (127 parts).

EXAMPLE 22

Methyl acetate (600 parts), lithium iodide (140 parts) and rhodium chloride hydrate (6 parts) are heated at 175° C. in a stirred stainless steel autoclave under an atmosphere of carbon monoxide (total pressure 350 p.s.i.g.; initial partial pressure of carbon monoxide 65 p.s.i.g.). After 8 hours reaction time a GC analysis of the reaction mixture shows it to contain 75.2% acetic anhydride (707 parts).

EXAMPLE 23

Methyl acetate (600 parts), methyl iodide (35 parts), lithium iodide (70 parts) and rhodium chloride hydrate (3 parts) are heated at 175° C. in a stirred stainless steel autoclave under an atmosphere of carbon monoxide (total pressure 350 p.s.i.g.; initial partial pressure of carbon monoxide 66 p.s.i.g.). After 8 hours reaction time a GC analysis of the reaction mixture shows it to contain 78.4% acetic anhydride (707 parts).

EXAMPLE 24

Methyl acetate (600 parts), lithium acetate (17 parts), lithium iodide (35 parts) and rhodium chloride hydrate (3 parts) are heated at 175° C. in a stirred stainless-steel autoclave under an atmosphere of carbon monoxide (total pressure 350 p.s.i.g.; initial partial pressure of carbon monoxide 66 p.s.i.g.). After 8 hours reaction time a GC analysis of the reaction mixture shows it to contain 68% acetic anhydride (528 parts).

EXAMPLE 25

Methyl acetate (300 parts), methyl iodide (35 parts) and iridium tri-chloride (2.2 parts) are heated at 225° C. in a stirred stainless-steel autoclave under an atmosphere of carbon monoxide (total pressure of the system 1000 p.s.i.g., carbon monoxide partial pressure 320 p.s.i.g.). After 14 hours reaction time GC analysis of the reaction mixture shows it to contain 22% acetic anhydride. The remainder of the reaction mixture is composed of unreacted reagents, reaction intermediates and catalyst.

EXAMPLE 26

Methyl acetate (6 parts), lithium iodide (0.7 parts) and platinum dibromide (0.1 part) are heated in an atmosphere of carbon monoxide (total pressure 630 p.s.i.g.; initial CO partial pressure 350 p.s.i.g.) at 175° C. for 16 hours in a rotating glass-lined pressure vessel. GC analysis of the reaction mixture shows that it contains 1.4% acetic anhydride (0.1 part).

EXAMPLE 27

Methyl acetate (6 parts), lithium iodide (0.2 part) and osmium chloride (0.1 part) are heated in an atmosphere of carbon monoxide (initial CO partial pressure 350 p.s.i.g.; total pressure 630 p.s.i.g.) at 175° C. for 16 hours in a rotating glass-lined pressure vessel. GC analysis of the reaction mixture shows that it contains 4.5% acetic anhydride (0.28 part).

EXAMPLE 28

Methyl acetate (150 parts), methyl iodide (18.5 parts), rhodium trichloride hydrate (0.75 part), chromium metal powder (1.0 part) and sodium methoxide (7.0 parts) are heated at 175° C. in a stirred glass-lined pressure vessel, under an atmosphere of carbon monoxide (total pressure 350 p.s.i.g.; CO partial pressure 70 p.s.i.g.). After 4 hours reaction time, GC analysis shows the reaction mixture to contain 22.5% acetic anhydride (41.5 parts).

EXAMPLE 29

Methyl acetate (150 parts), rhodium trichloride hydrate (0.75 part), molybdenum hexacarbonyl (1.5 parts), methyl iodide (16.0 parts) and lithium iodide (2.5 parts) are heated at 175° C. in a stirred glass-lined pressure vessel, under an atmosphere of carbon monoxide (total pressure 350 p.si.g.; CO partial pressure 70 p.s.i.g.). After 4 hours reaction time, GC analysis of the reaction mixture shows it to contain 40.0% acetic anhydride (82.7 parts).

EXAMPLE 30

Phenyl benzoate (150 parts), iodobenzene (5 parts), rhodium trichloride hydrate (0.75 parts), lithium iodide (8 parts), chromium metal powder (one part), and benzene (100 parts) are heated at 175° C. in a stirred pressure bessel, under an atmosphere of carbon monoxide (total pressure 500 p.si.g.; CO partial pressure 350 p.s.i.g.). After 10 hours reaction time, analysis of the reaction mixture shows it to contain 36% benzoic anhydride.

EXAMPLE 31

Heptylcaprylate (600 parts), rhodium trichloride hydrate (3 parts), lithium iodide (170 parts) and chromium metal powder (3 parts) are heated at 175° C. in a stirred stainless-steel autoclave under an atmosphere of carbon monoxide (total pressure 500 p.s.i.g.). After 12 hours reaction time, an analysis of the reaction mixture shows it to contain 24% carprylic anhydride (190 parts).

EXAMPLE 32

Dimethyl ether (190 parts), methyl acetate (300 parts), methyl iodide (74 parts) and rhodium trichloride (3 parts) are heated at 150° C. in a stirred stainless-steel autoclave under an atmosphere of carbon monoxide (total pressure 800 p.s.i.g.; CO partial pressure 120 p.s.i.g.). After 2 hours reaction time, GC analysis of the reaction mixture shows that it contains 76% methyl acetate (489 parts) and some acetic anhydride.

EXAMPLE 33

Dimethyl ether (375 parts), methyl iodide (75 parts) and rhodium trichloride hydrate (3 parts) are heated at 110° C. in a stirred stainless-steel autoclave under an atmosphere of carbon monoxide (total pressure 800 p.s.i.g.; CO partial pressure 190 p.s.i.g.). After 2 hours reaction time, GC analysis of the reaction mixture shows that it contains 16.3% methyl acetate (80 parts) and 2.4% acetic anhydride (12 parts).

EXAMPLE 34

Methyl acetate (150 parts) rodium trichloride hydrate (0.75 part), cerous iodide (24.7 parts) and chromium metal powder (1 part) are heated at 175° C. in a stirred glass-lined pressure vessel under an atmosphere of CO (total pressure 350 p.s.i.g.; CO partial pressure 70 p.s.i.g.). After 8 hours reaction time, GC analysis of the reaction mixture shows it to contain 22.1% of acetic anhydride (41.5 parts).

What is claimed is:

1. A process for the preparation of an anhydride of an alkanoic monocarboxylic acid which comprises reacting a feed consisting essentially of an alkanoic carboxylate ester or an alkyl hydrocarbyl ether or a mixture of said ester and said ether with carbon monoxide and a halide which is an iodide under substantially anhydrous conditions in the presence of a rhodium catalyst and in the presence of an added promoter for said catalyst at a temperature of 20° to 500° C. and under a carbon monoxide partial pressure of 0.1 to 15,000 psig, said promoter being a lithium compound.

2. A process for the preparation of an anhydride of an alkanoic monocarboxylic acid which comprises reacting a feed consisting essentially of an alkanoic carboxylate ester or an alkyl hydrocarbyl ether or a mixture of said ester and said ether with carbon monoxide and a halide which is an iodide under substantially anhydrous conditions in the presence of a rhodium catalyst and an added promoter for said catalyst at a temperature of 20° to 500° C. and under a carbon monoxide partial pressure of 0.1 to 15,000 psig, said promoter being a lithium salt.

3. A process as defined in claim 2, wherein said promoter is a lithium halide or a lithium carboxylate.

4. A process as defined in claim 3, wherein said promoter is lithium iodide or lithium acetate.

5. A process for the preparation of acetic anhydride acid which comprises reacting a feed consisting essentially of methyl acetate or dimethyl ether or a mixture of said ester and said ether with carbon monoxide and a halide which is methyl iodide under substantially anhydrous conditions in the presence of a rhodium catalyst and an added promoter for said catalyst at a temperature of 20° to 500° C. and under a carbon monoxide partial pressure of 0.1 to 15,000 psig, said promoter being a lithium compound.

6. A process as defined in claim 5, wherein said promoter is a lithium salt.

7. A process as defined in claim 6, wherein said promoter is a lithium halide or a lithium carboxylate.

8. A process as defined in claim 7, wherein said promoter is lithium iodide or lithium acetate.

9. A liquid-phase process for the preparation of an anhydride of an alkanoic monocarboxylic acid which comprises carbonylating a liquid-phase mixture consisting essentially of an alkanoic carboxylate ester or an alkyl hydrocarbyl ether, and an alkyl hydrocarbyl iodide in the presence of a rhodium catalyst and in the presence of an added promoter for said catalyst which is a lithium compound by reacting said liquid-phase mixture with carbon monoxide under substantially anhydrous conditions to produce said anhydride in admixture with said alkyl hydrocarbyl iodide, and recovering said anhydride from the reaction product, said carbonylation of said mixture being carried out at a temperature of 20–500° C. and said carbon monoxide being supplied under partial pressure of 0.1–15,000 psi.

10. A liquid-phase process for the preparation of acetic anhydride which comprises carbonylating a liquid-phase mixture comprising methyl acetate or dimethyl ether, and methyl iodide in the presence of a rhodium catalyst and an added promoter for said catalyst which is a lithium compound by reacting said liquid-phase mixture with carbon monoxide under substantially anhydrous conditions to produce said acetic anhydride in admixture with said methyl iodide, and recovering said acetic anhydride from the reaction product, said carbonylation of said mixture being carried out at a temperature of 20–500° C. and said carbon monoxide being supplied under partial pressure of 5–2000 psi, the ratio of said methyl acetate or said dimethyl ether to the iodide in the reaction system being 1 to 500 equivalents of said methyl acetate or said dimethyl ether per equivalent of iodide, and said promoter being present in the amount of 0.0001 mol to 100 mols per mol of rhodium catalyst.

11. A liquid-phase process for the preparation of acetic anhydride which comprises carbonylating a liquid-phase mixture comprising methyl acetate or dimethyl ether, and methyl iodide in the presence of a rhodium catalyst and an added promoter for said catalyst which is a lithium salt by reacting said liquid-phase mixture with carbon monoxide under substantially anhydrous conditions to produce said acetic anhydride in admixture with said methyl iodide, and recovering said acetic anhydride from the reaction product, said carbonylation of said mixture being carried out at a temperature of 20–500° C. and said carbon monoxide being supplied under partial pressure of 5–2000 psi, the ratio of said methyl acetate or said dimethyl ether to the iodide in the reaction system being 1 to 500 equivalents of said methyl acetate or said dimethyl ether per equivalent of iodide, and said promoter being present in the amount of 0.0001 mol to 100 mols per mol of rhodium catalyst.

12. A process as defined in claim 9, wherein said promoter is a lithium salt.

13. A process as defined in claim 9, wherein said promoter is a lithium halide or a lithium carboxylate.

14. A process as defined in claim 9, wherein said promoter is lithium iodide or lithium acetate.

15. A process as defined in claim 11, wherein said promoter is a lithium halide or a lithium carboxylate.

16. A process as defined in claim 11, wherein said promoter is lithium iodide or lithium acetate.

* * * * *